(12) United States Patent
Takahashi et al.

(10) Patent No.: US 9,932,417 B1
(45) Date of Patent: Apr. 3, 2018

(54) COMPOUND, MODIFIED POLYMER, RUBBER COMPOSITION, TIRE, AND CONVEYOR BELT

(71) Applicant: THE YOKOHAMA RUBBER CO., LTD., Minato-ku, Tokyo (JP)

(72) Inventors: Ryota Takahashi, Hiratsuka (JP); Manabu Kato, Hiratsuka (JP); Takahiro Okamatsu, Hiratsuka (JP); Yoshiaki Kirino, Hiratsuka (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 0 days.

(21) Appl. No.: 15/554,930

(22) PCT Filed: Mar. 16, 2016

(86) PCT No.: PCT/JP2016/058352
§ 371 (c)(1),
(2) Date: Aug. 31, 2017

(87) PCT Pub. No.: WO2016/148198
PCT Pub. Date: Sep. 22, 2016

(30) Foreign Application Priority Data

Mar. 17, 2015 (JP) .................. 2015-053243

(51) Int. Cl.
| | |
|---|---|
| *C08C 19/22* | (2006.01) |
| *C07C 291/02* | (2006.01) |
| *C08K 3/04* | (2006.01) |
| *B60C 1/00* | (2006.01) |
| *B65G 15/32* | (2006.01) |

(52) U.S. Cl.
CPC ............ *C08C 19/22* (2013.01); *C07C 291/02* (2013.01); *C08K 3/04* (2013.01); *B60C 1/0016* (2013.01); *B65G 15/32* (2013.01); *B65G 2812/02198* (2013.01); *C07C 2601/16* (2017.05)

(58) Field of Classification Search
CPC ..... C08C 19/22; C08G 65/333; C07C 291/02; C08F 8/30
See application file for complete search history.

(56) References Cited

U.S. PATENT DOCUMENTS

| | | |
|---|---|---|
| 5,310,620 A | 5/1994 | Watanabe et al. |
| 9,493,599 B2 | 11/2016 | Takahashi et al. |

FOREIGN PATENT DOCUMENTS

| | | |
|---|---|---|
| JP | H05-208949 A | 8/1993 |
| JP | 2008-163232 A | 7/2008 |
| JP | 2013-032471 A | 2/2013 |
| JP | 2014-101400 A | 6/2014 |
| JP | 2015-044929 A | 3/2015 |

*Primary Examiner* — Peter D. Mulcahy
(74) *Attorney, Agent, or Firm* — Carrier Blackman & Associates, P.C.; Joseph P. Carrier; William D. Blackman

(57) ABSTRACT

The present invention is to provide a compound that can provide a modified polymer exhibiting excellent rigidity, wear resistance, and low heat build-up when used in a rubber composition; a modified polymer obtained by subjecting a polymer to modification with the compound; a rubber composition including the modified polymer; and a tire and a conveyor belt that are produced by using the rubber composition. The compound of the present invention is represented by Formula (M) below.

(M)

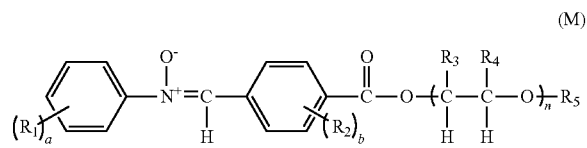

20 Claims, 1 Drawing Sheet

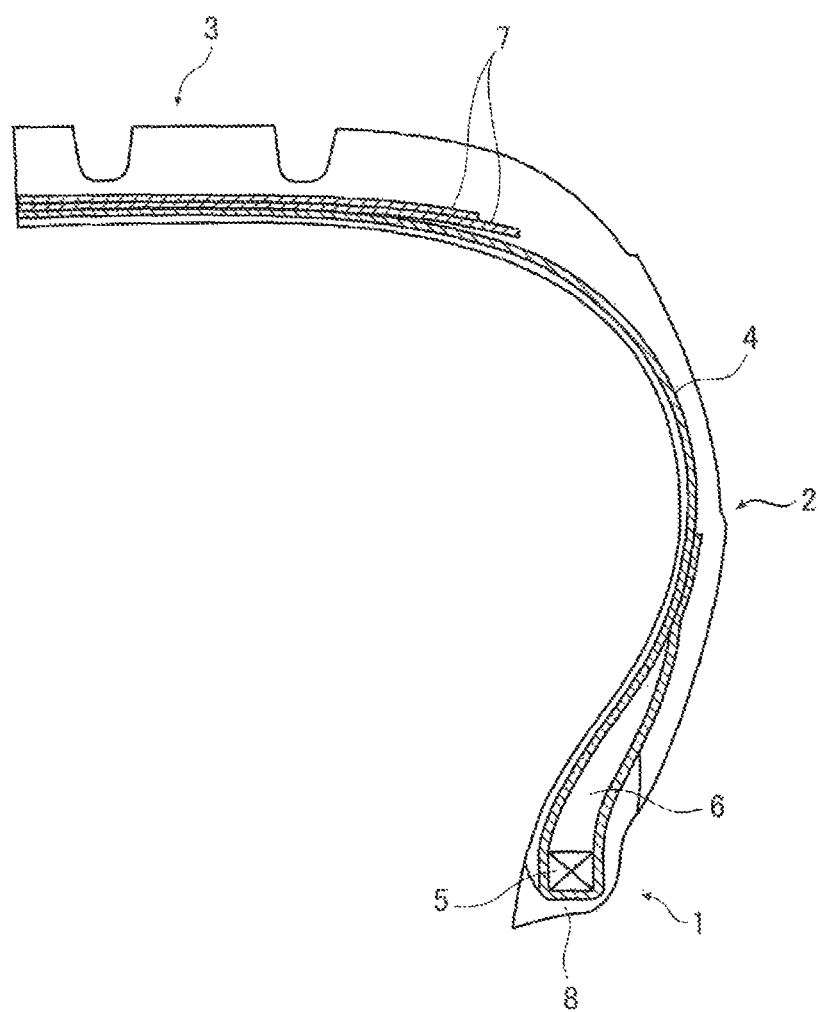

COMPOUND, MODIFIED POLYMER, RUBBER COMPOSITION, TIRE, AND CONVEYOR BELT

TECHNICAL FIELD

The present invention relates to a compound, a modified polymer, a rubber composition, a tire, and a conveyor belt.

BACKGROUND ART

Conventionally, compounds having a nitrone group have been known as modifying agents to modify polymers used in rubber members of tires or the like.

For example, Patent Document 1 discloses a nitrone compound having a nitrogen-containing heterocycle in a molecule as a modifying agent for modifying butadiene rubbers.

CITATION LIST

Patent Literature

Patent Document 1: JP-A-2013-32471

SUMMARY OF INVENTION

Technical Problem

Recently, further enhancement in rigidity and wear resistance of the rubber composition after vulcanization has been demanded as even higher wear resistance has been demanded for rubber members such as tires and conveyor belts. From the perspective of environmental concerns, reduction in heat build-up has been demanded along with demand in enhancement in fuel economy.

In such circumstances, when the inventors of the present invention have synthesized a compound having a nitrone group (nitrone compound) with reference to Patent Document 1 and studied a modified polymer obtained by performing modification with the compound, the inventors found that further enhancement of rigidity and wear resistance of the obtained rubber composition is desired, taking future increase in the level required for the durability into consideration. Also, the present inventors found that the synthesized compound did not necessarily meet the current requirements for low heat build-up.

Therefore, in the light of such circumstances, an object of the present invention is to provide a composition that can provide a modified polymer exhibiting excellent rigidity, wear resistance, and low heat build-up when used in a rubber composition; a modified polymer obtained by subjecting a polymer to modification with the compound; a rubber composition including the modified polymer; and a tire and a conveyor belt that are produced by using the rubber composition.

Solution to Problem

As a result of diligent research for the problems, the inventors of the present invention found that the problems described above can be solved by using polyethylene glycol or polypropylene glycol having a nitrone group in a molecule as a modifying agent, and thus completed the present invention.

Specifically, the inventors found that the object described above can be achieved by the following features.

(1) A compound represented by Formula (M) below.

(2) The compound according to (1) above, where the compound is obtained by reacting a nitrone compound with at least one type of polyether selected from the group consisting of polyethylene glycol and polypropylene glycol, and a molecular weight of the polyether is from 150 to 2000.

(3) A modified polymer obtained by subjecting a polymer to modification with the compound described in (1) or (2) above.

(4) The modified polymer according to (3) above, where the polymer is at least one type of conjugated diene polymer selected from the group consisting of SBR, BR, IR, NR, and NBR.

(5) A rubber composition including the modified polymer described in (3) or (4) above.

(6) The rubber composition according to (5) above, where
the rubber composition comprises a diene rubber and a carbon black;
the diene rubber includes the modified polymer; and
a content of the modified polymer in the diene rubber is from 15 to 70 mass %.

(7) A tire produced by using the rubber composition described in (5) or (6) above.

(8) A conveyor belt produced by using the rubber composition described in (5) or (6) above.

Advantageous Effects of Invention

As described below, according to the present invention, a compound that can provide a modified polymer exhibiting excellent rigidity, wear resistance, and low heat build-up when used in a rubber composition; a modified polymer obtained by subjecting a polymer to modification with the compound; a rubber composition including the modified polymer; and a tire and a conveyor belt that are produced by using the rubber composition can be provided.

BRIEF DESCRIPTION OF DRAWINGS

FIG. 1 is a partial cross-sectional schematic view of a tire that represents one embodiment of the tire of the present invention.

DESCRIPTION OF EMBODIMENTS

Hereinafter, the compound of the present invention, the modified polymer of the present invention, the rubber composition of the present invention, and the manufactured tire or the like using the rubber composition of the present invention are described.

Note that, in the present specification, numerical ranges indicated using "(from) . . . to . . . " include the former number as the lower limit value and the later number as the upper limit value.

Compound

The compound of the present invention is a compound represented by Formula (M) below (hereinafter, also referred to as "particular compound").

It is conceived that, because the compound of the present invention has a structure represented by Formula (M) below, predetermined effects can be achieved. Although the reason for this is unknown, the reason is presumed to be as follows.

In the case where a polymer is subjected to modification with the compound of the present invention (particular compound), the obtained modified polymer has a nitrone residue (nitrone group after the modification) and a polyether structure ($-CHR_3-CHR_4-O-$). Note that a uniform network of the modified polymers is formed due to the interaction between the nitrone residue and the polyether structure. As a result, it is conceived that the obtained rubber composition exhibits excellent rigidity and wear resistance after the vulcanization. Furthermore, as described above, it is conceived that, because the uniform structure is formed, energy loss is reduced and low heat build-up characteristics is improved. Furthermore, in the case where a filler such as carbon black or silica is present in the rubber composition, the modified polymer also interacts with the filler and forms a fine and uniform network. As a result, even in the case where a filler such as carbon black or silica is present in the rubber composition, it is conceived that excellent rigidity, wear resistance, and low heat build-up are exhibited.

[Chemical Formula 1]

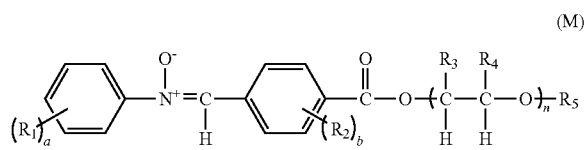

(M)

In Formula (M), $R_1$ and $R_2$ each independently represent a hydrogen atom or a substituent. $R_3$ and $R_4$ represent a hydrogen atom or a methyl group. However, if $R_3$ is a methyl group, $R_4$ represents a hydrogen atom, and if $R_4$ is a methyl group, $R_3$ represents a hydrogen atom. $R_5$ represents a hydrogen atom or a hydrocarbon group. a represents an integer of 0 or 1 to 5. b represents an integer of 0 or 1 to 4. n represents a number of 2 or greater.

As described above, in Formula (M), $R_1$ and $R_2$ each independently represent a hydrogen atom or a substituent. Among these, a hydrogen atom is preferable.

The substituent is not particularly limited as long as the substituent is a monovalent substituent. Examples thereof include hydrocarbon groups that may have a halogen atom, a hydroxy group, a nitro group, a carboxy group, an alkoxy group, an amino group, a mercapto group, an acyl group, an imide group, a phosphino group, a phosphinyl group, a silyl group, or a hetero atom.

Examples of the halogen atom include a fluorine atom, a chlorine atom, a bromine atom, and an iodine atom.

Examples of the hetero atom of the hydrocarbon group that may have a hetero atom include an oxygen atom, a nitrogen atom, a sulfur atom, and a phosphorous atom.

Examples of the hydrocarbon group of the hydrocarbon group that may have a hetero atom include aliphatic hydrocarbon groups, aromatic hydrocarbon groups, and groups that have a combination of these.

The aliphatic hydrocarbon group may be in a form of straight-chain, branched-chain, or ring. Specific examples of the aliphatic hydrocarbon group include straight-chain or branched alkyl groups (especially, those having from 1 to 30 carbons), straight-chain or branched alkenyl groups (especially, those having from 2 to 30 carbons), and straight-chain or branched alkynyl groups (especially, those having from 2 to 30 carbons).

Examples of the aromatic hydrocarbon group include aromatic hydrocarbon groups having from 6 to 18 carbons, such as a phenyl group, a tolyl group, a xylyl group, and a naphthyl group.

As described above, in Formula (M), $R_3$ and $R_4$ represent a hydrogen atom or a methyl group. However, if $R_3$ is a methyl group, $R_4$ represents a hydrogen atom, and if $R_4$ is a methyl group, $R_3$ represents a hydrogen atom. Both of $R_3$ and $R_4$ are preferably hydrogen atoms.

As described above, in Formula (M), $R_5$ represents a hydrogen atom or a hydrocarbon group.

Specific examples and preferred aspects of the hydrocarbon group are as described above.

As described above, a represents an integer of 0 or 1 to 5. A plurality of $R_1$ moieties that are present in the case where a is an integer of 2 or greater may be the same or different.

As described above, b represents an integer of 0 or 1 to 4. A plurality of $R_2$ moieties that are present in the case where b is an integer of 2 or greater may be the same or different.

As described above, in Formula (M), n represents a number of 2 or greater. Among these, a number of from 2 to 100 is preferable, and a number of from 3 to 50 is more preferable.

Note that, when n has a distribution, n represents an average value. For example, 1 mole of an aspect of n=2 and 1 mol of an aspect of n=4 are present, n is 3 ($=(2 \times 1 + 4 \times 1) \div 2$).

Preferred Embodiment

The particular compound is preferably a compound obtained by reacting a nitrone compound with at least one type of polyether selected from the group consisting of polyethylene glycol and polypropylene glycol.

Raw materials are described below.
Nitrone Compound

The nitrone compound is a compound having a nitrone group represented by Formula (1) below.

[Chemical Formula 2]

Formula (1)

In Formula (1), * indicates a bonding position.

The nitrone compound described above is preferably a compound represented by Formula (2) below.

[Chemical Formula 3]

Formula (2)

In Formula (2) above, X and Y each independently represent an aliphatic hydrocarbon group, an aromatic hydrocarbon group, or an aromatic heterocycle group that may have a substituent.

Examples of the aliphatic hydrocarbon group represented by X or Y include alkyl groups, cycloalkyl groups, and alkenyl groups. Examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, a 1-methylbutyl group, a 2-methylbutyl group, a 1,2-dimethylpropyl group, an n-hexyl group, an n-heptyl group, and an n-octyl group. Among these, alkyl groups having from 1 to 18 carbons are preferable, and alkyl groups having from 1 to 6 carbons are more preferable. Examples of the cycloalkyl groups include cyclopropyl groups, cyclobutyl groups, cyclopentyl groups, and cyclohexyl groups. Among these, cycloalkyl groups having from 3 to 10 carbons are preferable, and cycloalkyl groups having from 3 to 6 carbons are more preferable. Examples of the alkenyl groups include vinyl groups, 1-propenyl groups, allyl groups, isopropenyl groups, 1-butenyl groups, and 2-butenyl groups. Among these, alkenyl groups having from 2 to 18 carbons are preferable, and alkenyl groups having from 2 to 6 carbons are more preferable.

Examples of the aromatic hydrocarbon group represented by X or Y include aryl groups, and aralkyl groups.

Examples of the aryl group include a phenyl group, a naphthyl group, an anthryl group, a phenanthryl group, and a biphenyl group. Among these, aryl groups having from 6 to 14 carbons are preferable, aryl groups having from 6 to 10 carbons are more preferable, and a phenyl group and a naphthyl group are even more preferable.

Examples of the aralkyl group include a benzyl group, a phenethyl group, and a phenylpropyl group. Among these, aralkyl groups having from 7 to 13 carbons are preferable, aralkyl groups having from 7 to 11 carbons are more preferable, and a benzyl group is even more preferable.

Examples of the aromatic heterocycle group represented by X or Y include a pyrrolyl group, a furyl group, a thienyl group, a pyrazolyl group, an imidazolyl group (an imidazole group), an oxazolyl group, an isoxazolyl group, a thiazolyl group, an isothiazolyl group, a pyridyl group (a pyridine group), a furan group, a thiophene group, a pyridazinyl group, a pyrimidinyl group, and a pyrazinyl group. Among these, a pyridyl group is preferable.

The substituents that may be included in the group represented by X or Y is not particularly limited, and examples thereof include an alkyl group having from 1 to 4 carbons, a hydroxy group, an amino group, a nitro group, a carboxy group, a sulfonyl group, an alkoxy group, a halogen atom, and the like. Among these, a carboxy group is preferable.

Note that examples of the aromatic hydrocarbon group having such a substituent include aryl groups having a substituent, such as a tolyl group and a xylyl group; aralkyl groups having a substituent, such as a methylbenzyl group, an ethylbenzyl group, and a methylphenethyl group.

The nitrone compound described above is preferably a compound represented by Formula (3) below.

[Chemical Formula 4]

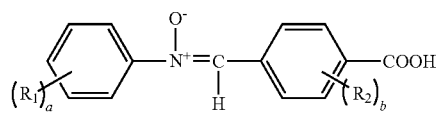

(3)

In Formula (3), definitions, specific examples, and preferred aspects of $R_1$, $R_2$, a, and b are the same as those described for $R_1$, $R_2$, a, and b of Formula (M) described above, respectively.

Synthesis of Nitrone Compound

The method of the nitrone compound synthesis is not particularly limited, and conventionally known methods can be used. For example, a compound (carboxynitrone) having a carboxy group and a nitrone group can be obtained by stirring a compound having a hydroxyamino group (—NHOH) and a compound having an aldehyde group (—CHO) and a carboxy group at a molar ratio of hydroxyamino group to aldehyde group (—NHOH/—CHO) of from 1.0 to 1.5 in the presence of an organic solvent (e.g. methanol, ethanol, or tetrahydrofuran) at room temperature for 1 to 24 hours to allow the both groups to react.

Polyether

The polyether is at least one type of polyether selected from the group consisting of polyethylene glycol and polypropylene glycol.

The polyethylene glycol is preferably a compound represented by Formula (4) below.

[Chemical Formula 5]

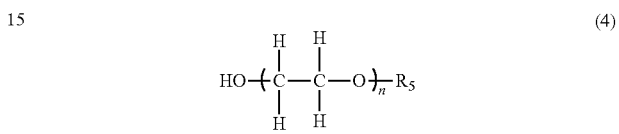

(4)

In Formula (4), definitions, specific examples, and preferred aspects of $R_5$ and n are the same as those described for $R_5$ and n of Formula (M) described above, respectively.

The polypropylene glycol is preferably a compound represented by Formula (5) below.

[Chemical Formula 6]

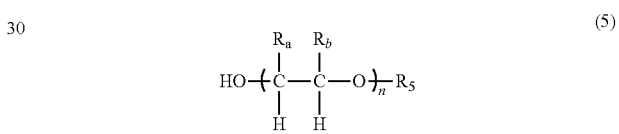

(5)

In Formula (5), definitions, specific examples, and preferred aspects of $R_5$ and n are the same as those described for $R_5$ and n of Formula (M) described above, respectively.

In Formula (5), $R_a$ and $R_b$ represent a hydrogen atom or a methyl group. However, if $R_a$ is a hydrogen atom, $R_b$ represents a methyl group, and if $R_a$ is a methyl group, $R_b$ represents a hydrogen atom.

Although the molecular weight of the polyether is not particularly limited, the molecular weight is preferably from 150 to 2000, and more preferably from 400 to 1000. Note that, when the molecular weight has a distribution, the molecular weight represents an average value (average molecular weight). For example, when 1 mole of an aspect with the molecular weight of 200 and 1 mole of an aspect with the molecular weight of 300 are present, the molecular weight is 250 (=(200×1+300×1)÷2).

Synthesis of Particular Compound

The method of synthesis of the particular compound is not particularly limited, and conventionally known methods can be used. Among these, a method in which a nitrone compound is reacted with at least one type of polyether selected from the group consisting of polyethylene glycol and polypropylene glycol is preferable. The nitrone compound and the polyether are as described above.

Modified Polymer

The modified polymer of the present invention is a modified polymer obtained by subjecting a polymer to modification with the particular compound described above.

Polymer

The polymer to be modified is not particularly limited; however, the polymer is preferably a conjugated diene polymer.

The conjugated diene polymer is not particularly limited, and examples thereof include a natural rubber (NR), an isoprene rubber (IR), a butadiene rubber (BR), an aromatic vinyl-conjugated diene copolymer rubber (e.g. SBR), an acrylonitrile-butadiene copolymer rubber (NBR), a butyl rubber (IIR), a halogenated butyl rubber (Br-IIR, Cl-IIR), and a chloroprene rubber (CR). Among these, at least one type of conjugated diene polymer selected from the group consisting of SBR, BR, IR, NR, and NBR is preferable. Among these, BR or SBR is preferable.

Method of Production of Modified Polymer

The method of subjecting a polymer to modification with the particular compound described above is not particularly limited. Examples of the method include a method in which the polymer and the particular compound are mixed at from 100° C. to 200° C. for from 1 to 30 minutes.

For example, in the case where the polymer is a conjugated diene polymer, a cycloaddition reaction occurs between the double bond derived from the conjugated diene included in the conjugated diene polymer and the nitrone group included in the particular compound to form a five-membered ring as described in Formula (6) below or Formula (7) below. Note that Formula (6) below represents a reaction between a 1,4-bond and a particular compound, and Formula (7) below represents a reaction between a 1,2-vinyl bond and a particular compound. Furthermore, Formulas (6) and (7) represent reactions for the conjugated diene polymer in the case where butadiene (1,3-butadiene) is used as the conjugated diene monomer; however, even if the conjugated diene monomer is other than butadiene, the five-membered ring can be obtained by a similar reaction.

[Chemical Formula 7]

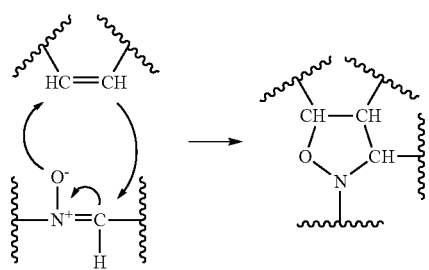

Formula (6)

[Chemical Formula 8]

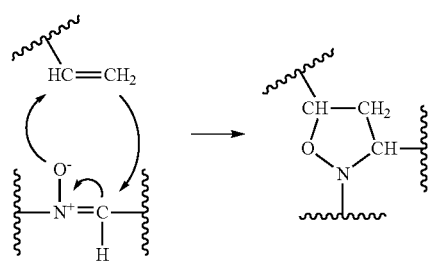

Formula (7)

When the polymer is a conjugated diene polymer, the amount of the particular compound reacted with the double bonds of the conjugated diene polymer is not particularly limited, but is preferably from 0.1 to 10 parts by mass, and more preferably from 0.3 to 3 parts by mass, per 100 parts by mass of the conjugated diene polymer.

Degree of Modification

When the polymer is a conjugated diene polymer, the degree of modification of the modified polymer is not particularly limited, but is preferably from 0.02 to 4.0 mol %, and more preferably from 0.05 to 2.0 mol %.

Here, "degree of modification" refers to the proportion (mol %) of the double bonds modified with the particular compound to all the double bonds in the conjugated diene (conjugated diene unit) included in the conjugated diene polymer. For example, in the case of a conjugated diene polymer using butadiene (1,3-butadiene) as the conjugated diene monomer, the degree of modification represents the proportion (mol %) of formation of the structure represented by Formula (6) or (7) above through the modification with the particular compound. The degree of modification, for example, can be determined by NMR measurement of the conjugated diene polymer and the modified polymer (i.e. the polymers before and after the modification).

Note that in this specification, a modified polymer having a degree of modification of 100 mol % falls under the category of a diene rubber.

Rubber Composition

The rubber composition of the present invention (hereinafter, also referred to "composition of the present invention") includes the modified polymer of the present invention described above.

Among these, a diene rubber including the modified polymer of the present invention described above is preferably included.

Diene Rubber

The diene rubber may include a rubber component in addition to the modified polymer. Such a rubber component is not particularly limited; however, examples thereof include a natural rubber, an isoprene rubber (IR), a butadiene rubber (BR), an aromatic vinyl-conjugated diene copolymer rubber (e.g. styrene-butadiene rubber (SBR)), an acrylonitrile-butadiene copolymer rubber (NBR), a butyl rubber (IIR), a halogenated butyl rubber (Br-IIR, Cl-IIR), and a chloroprene rubber (CR).

The content of the modified polymer in the diene rubber is not particularly limited; however, the content is preferably from 10 to 80 mass %, more preferably from 15 to 70 mass %, and even more preferably from 15 to 40 mass %.

Carbon Black

The composition of the present invention preferably includes carbon black.

The carbon black is not particularly limited and, for example, carbon blacks of various grades, such as SAF-HS, SAF, ISAF-HS, ISAF, ISAF-LS, IISAF-HS, HAF-HS, HAF, HAF-LS, FEF, GPF, and SRF, can be used.

The content of the carbon black in the composition of the present invention is not particularly limited, but is preferably from 10 to 80 parts by mass, and more preferably from 20 to 50 parts by mass, per 100 parts by mass of the diene rubber described above.

Silica

The composition of the present invention preferably includes silica.

The silica is not particularly limited, and any conventionally known silica that is blended in rubber compositions for use in tires or the like can be used.

Specific examples of the silica include wet silica, dry silica, fumed silica, and diatomaceous earth. Among these, wet silica is preferable. One type of the silica may be used alone, or two or more types of the silicas may be used in combination.

In the composition of the present invention, the content of the silica is not particularly limited but is preferably from 25 to 130 parts by mass, and more preferably from 40 to 80 parts by mass, per 100 parts by mass of the diene rubber.

Optional Component

The composition of the present invention may further include additives as necessary within a scope that does not inhibit the effect or purpose thereof.

Examples of the additives include various additives that are typically used in rubber compositions, such as fillers, silane coupling agents, zinc oxide (flower of zinc), stearic acid, adhesive resin, peptizing agent, anti-aging agents, wax, processing aids, aroma oils, liquid polymers, terpene resins, thermosetting resins, vulcanizing agents (e.g. sulfur), and vulcanization accelerators.

Method of Producing Rubber Composition

The method of producing the composition of the present invention is not particularly limited, and specific examples thereof include a method whereby each of the above-mentioned components is kneaded using a publicly known method and device (e.g. Banbury mixer, kneader, and roll). When the composition of the present invention includes a sulfur or a vulcanization accelerator, the components other than the sulfur and the vulcanization accelerator are preferably blended first at a high temperature (preferably from 80 to 140° C.) and then cooled before the sulfur or the vulcanization accelerator is blended.

In addition, the composition of the present invention can be vulcanized or crosslinked under conventionally known vulcanizing or crosslinking conditions.

Application

The composition of the present invention can be suitably used in production of rubber members, such as tires (preferably, tire tread portions and sidewall portions) and conveyor belts.

Tire

The tire of the present invention is a tire produced using the composition of the present invention described above. Among these, a pneumatic tire in which the composition of the present invention is used in a tire tread portion and/or a sidewall portion is preferred.

FIG. 1 is a schematic partial cross-sectional view of a tire that illustrates one embodiment of a tire of the present invention, but the tire of the present invention is not limited to the embodiment illustrated in FIG. 1.

In FIG. 1, reference sign 1 denotes a bead portion, reference sign 2 denotes a sidewall portion, and reference sign 3 denotes a tire tread portion.

In addition, a carcass layer 4, in which a fiber cord is embedded, is mounted between a left-right pair of bead portions 1, and ends of the carcass layer 4 are wound by being folded around bead cores 5 and a bead filler 6 from an inner side to an outer side of the tire.

In the tire tread portion 3, a belt layer 7 is provided along the entire circumference of the tire on the outer side of the carcass layer 4.

Additionally, rim cushions 8 are provided in parts of the bead portions 1 that are in contact with a rim.

Note that the tire tread portion 3 and/or the sidewall portion 2 are formed from the composition of the present invention described above.

The tire of the present invention can be produced, for example, in accordance with a conventionally known method. In addition to ordinary air or air with an adjusted oxygen partial pressure, inert gases such as nitrogen, argon, and helium can be used as the gas with which the tire is filled.

Conveyor Belt

The conveyor belt of the present invention is a conveyor belt for industrial use produced using the composition of the present invention described above.

EXAMPLES

Embodiments of the present invention are described in further detail below. However, the present invention is not limited to these embodiments.

Synthesis of Particular Compound (Particular Compound 1)

In a 2 L eggplant-shaped flask, methanol heated to 40° C. (900 mL) was placed, and then terephthalaldehydic acid represented by Formula (b-1) below (30.0 g) was added and dissolved. To this solution, a solution in which phenylhydroxylamine represented by Formula (a-1) below (21.8 g) was dissolved in methanol (100 mL) was added and stirred at room temperature for 19 hours. After the completion of stirring, a nitrone compound (carboxynitrone) represented by formula (c-1) below was obtained by recrystallization from methanol (41.7 g). The yield was 86%.

The obtained carboxynitrone (5.3 g), polyethylene glycol represented by Formula (d-1) below (n: 3; molecular weight: 164) (15.5 g), and dimethylaminopyridine (0.25 g) were dissolved in dimethylformamide (45 mL), and then dicyclohexylcarbodiimide (5.0 g) was added thereto to perform reaction at 0° C. for 6 hours. Then, 100 mL of water was added to terminate the reaction, formed solids were removed, and the aqueous layer was extracted with 150 mL of ethyl acetate. Furthermore, washing was performed by 1 N of hydrochloric acid, 1 N of sodium hydroxide aqueous solution, and saturated salt solution to distill off the solvent to synthesize a compound represented by Formula (m1) below (n: 3) (7.5 g; yield: 88%). The obtained compound was used as the particular compound 1.

$^1$H-NMR (400 MHz, CDCl$_3$): δ 8.45 (d, 2H), 8.15 (d, 2H), 8.00 (s, 1H), 7.78 (m, 2H), 7.51 (m, 3H), 4.51 (t, 2H), 3.86 (t, 2H), 3.75 (m, 2H), 3.69 (m, 4H), 3.55 (t, 2H), 3.37 (s, 3H)

[Chemical Formula 9]

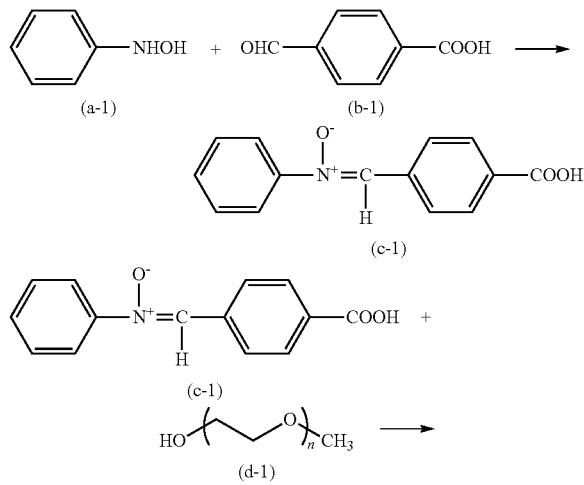

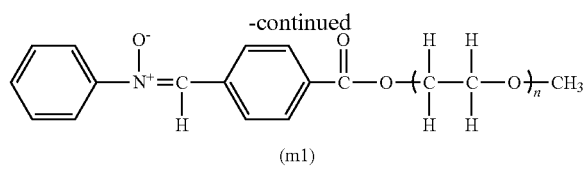

(m1)

Synthesis of Particular Compound (Particular Compound 2)

A compound represented by Formula (m1) above (n (average value): 8.4) was synthesized in accordance with the same procedure as that for the particular compound 1 except for using polyethylene glycol represented by Formula (d-1) above (n (average value): 8.4; average molecular weight: 400) in place of the polyethylene glycol represented by Formula (d-1) above (n: 3; molecular weight: 164). The obtained compound was used as the particular compound 2.

$^1$H-NMR (400 MHz, CDCl$_3$): δ 8.43 (d, 2H), 8.15 (d, 2H), 8.00 (s, 1H), 7.79 (m, 2H), 7.52 (m, 3H), 4.50 (t, 2H), 3.86 (t, 2H), 3.69 (m, 33.4H), 3.54 (t, 2H), 3.37 (s, 3H)

Synthesis of Particular Compound (Particular Compound 3)

A compound represented by Formula (m1) above (n (average value): 22) was synthesized in accordance with the same procedure as that for the particular compound 1 except for using polyethylene glycol represented by Formula (d-1) above (n (average value): 22; average molecular weight: 1000) in place of the polyethylene glycol represented by Formula (d-1) above (n: 3; molecular weight: 164). The obtained compound was used as the particular compound 3.

$^1$H-NMR (400 MHz, CDCl$_3$): δ 8.43 (d, 2H), 8.16 (d, 2H), 8.03 (s, 1H), 7.80 (m, 2H), 7.51 (m, 3H), 4.50 (t, 2H), 3.86 (t, 2H), 3.69 (m, 82H), 3.54 (t, 2H), 3.37 (s, 3H)

Synthesis of Comparative Compound

A compound represented by Formula (X) below was synthesized in accordance with the same procedure as that for the particular compound 1 except for using methanol in place of the polyethylene glycol represented by Formula (d-1) above. The obtained compound was used as the comparative compound.

[Chemical Formula 10]

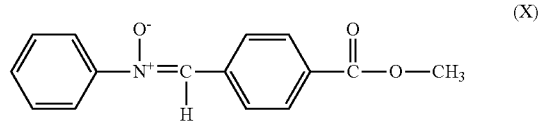

Synthesis of Modified Polymer (Modified Polymer 11)

The butadiene rubber (Nipol BR1220, manufactured by Zeon Corporation) was charged in a Banbury mixer at 120° C. and masticated for two minutes. Then, 3 parts by mass of the particular compound 1 synthesized as described above was charged per 100 parts by mass of the butadiene rubber and the mixture was blended for 5 minutes at 160° C. Thus, the butadiene rubber was modified with the particular compound (particular compound 1). The obtained modified polymer was used as the modified polymer 11.

When NMR measurement was performed for the obtained modified polymer 11 to determine the degree of modification, the degree of modification of the modified polymer 11 was 0.25 mol %.

Synthesis of Modified Polymer (Modified Polymer 12)

A butadiene rubber was modified with the particular compound (particular compound 2) in accordance with the same procedure as that for the modified polymer 11 except for charging 3 parts by mass of the particular compound 2 synthesized as described above in place of the particular compound 1. The obtained modified polymer was used as the modified polymer 12.

When NMR measurement was performed for the obtained modified polymer 12 to determine the degree of modification, the degree of modification of the modified polymer 12 was 0.15 mol %.

Synthesis of Modified Polymer (Modified Polymer 13)

A butadiene rubber was modified with the particular compound (particular compound 3) in accordance with the same procedure as that for the modified polymer 11 except for charging 3 parts by mass of the particular compound 3 synthesized as described above in place of the particular compound 1. The obtained modified polymer was used as the modified polymer 13.

When NMR measurement was performed for the obtained modified polymer 13 to determine the degree of modification, the degree of modification of the modified polymer 13 was 0.08 mol %.

Synthesis of Comparative Modified Polymer 1

A butadiene rubber was modified with the comparative compound in accordance with the same procedure as that for the modified polymer 11 except for charging 3 parts by mass of the comparative compound synthesized as described above in place of the particular compound 1. The obtained butadiene rubber modified with the comparative compound was used as a comparative modified polymer 1.

When NMR measurement was performed for the obtained comparative modified polymer 1 to determine the degree of modification, the degree of modification of the comparative modified polymer was 0.38 mol %.

Synthesis of Modified Polymer (Modified Polymer 21)

SBR (Tufdene E580, manufactured by Asahi Kasei Chemicals Corporation) was charged in a Bunbury mixer at 120° C. and masticated for 2 minutes. Then, 0.85 parts by mass of the particular compound 1 synthesized as described above was charged per 100 parts by mass of the SBR (100 parts by mass in terms of net amount of the rubber except the extender oil) and the mixture was blended for 5 minutes at 160° C. Thus, the SBR was modified with the particular compound (particular compound 1). The obtained modified polymer was used as the modified polymer 21.

When NMR measurement was performed for the obtained modified polymer 21 to determine the degree of modification, the degree of modification of the modified polymer 21 was 0.12 mol %.

Note that the modified polymer 21 was an oil extended product, and the oil extender content was 37.5 mass %.

Synthesis of Modified Polymer (Modified Polymer 22)

A SBR was modified with the particular compound (particular compound 2) in accordance with the same procedure as that for the modified polymer 21 except for charging 0.85 parts by mass of the particular compound 2 synthesized as described above in place of the particular compound 1. The obtained modified polymer was used as the modified polymer 22.

When NMR measurement was performed for the obtained modified polymer 22 to determine the degree of modification, the degree of modification of the modified polymer 22 was 0.07 mol %.

Note that the modified polymer 22 was an oil extended product, and the oil extender content was 37.5 mass %.

Synthesis of Modified Polymer (Modified Polymer 23)

A SBR was modified with the particular compound (particular compound 2) in accordance with the same procedure as that for the modified polymer 21 except for charging 0.85 parts by mass of the particular compound 3 synthesized as described above in place of the particular compound 1. The obtained modified polymer was used as the modified polymer 23.

When NMR measurement was performed for the obtained modified polymer 23 to determine the degree of modification, the degree of modification of the modified polymer 23 was 0.04 mol %.

Note that the modified polymer 23 was an oil extended product, and the oil extender content was 37.5 mass %.

Synthesis of Comparative Modified Polymer 2

A SBR was modified with the comparative compound in accordance with the same procedure as that for the modified polymer 21 except for charging 0.85 parts by mass of the comparative compound synthesized as described above in place of the particular compound 1. The obtained SBR modified with the comparative compound was used as a comparative modified polymer 2.

When NMR measurement was performed for the obtained comparative modified polymer 2 to determine the degree of modification, the degree of modification of the modified polymer 23 was 0.19 mol %.

Note that the comparative modified polymer 2 was an oil extended product, and the oil extender content was 37.5 mass %.

Preparation of Rubber Composition

The components shown in Tables 1-1 and 1-2 below were blended in the proportions (part by mass) shown in Tables 1-1 and 1-2 below.

Specifically, the components shown in Tables 1-1 and 1-2 below except for the sulfur and the vulcanization accelerator were first mixed in a Bunbury mixer at 80° C. for 5 minutes. Thereafter, a roll was used to mix the sulfur and the vulcanization accelerator to obtain a rubber composition.

Note that, in Tables 1-1 and 1-2, for items for which two numerical values are listed, an amount of the oil extended product is indicated as the value listed in the upper row (unit: part by mass) and a net amount of the rubber excluding the extender oil is indicated as the value listed in the bottom row (unit: part by mass).

Preparation of Vulcanized Rubber Sheet

A vulcanized rubber sheet was prepared by press-vulcanizing each of the obtained (unvulcanized) rubber compositions for 15 minutes at 160° C. in a mold (15 cm×15 cm×0.2 cm).

Evaluation

Modulus

The produced vulcanized rubber sheet was cut out into a dumbbell shape (No. 3 dumbbell shape) having a thickness of 2 mm and used as a test piece.

The 100% modulus (stress at 100% elongation) [MPa] of the obtained test piece was measured in accordance with JIS K6251:2010. The results are shown in Tables 1-1 and 1-2 (M100). Note that, for Table 1-1, the result was expressed as an index value with the M100 of Comparative Example 1-1 expressed as an index value of 100. Furthermore, for Table 1-2, the result was expressed as an index value with the M100 of Comparative Example 2-1 expressed as an index value of 100. A larger M100 indicates superior rigidity.

Wear Resistance

For the produced vulcanized rubber sheet, abrasion loss was measured in accordance with JIS K6264-1 2:2005 using a Lambourn abrasion tester (manufactured by Iwamoto Seisakusho) at a temperature of 20° C. and at a slip ratio of 50%.

The results are shown in Table 1.

For Table 1-1, the result was expressed as an index value obtained using the following formula, with the amount of wear of Comparative Example 1-1 expressed as an index of 100. A larger index value indicates a smaller amount of wear and excellent wear resistance.

Wear resistance=(amount of wear of Comparative Example 1-1/amount of wear of sample)×100

Furthermore, for Table 1-2, the result was expressed as an index value obtained using the following formula, with the amount of wear of Comparative Example 2-1 expressed as an index of 100. A larger index value indicates a smaller amount of wear and excellent wear resistance.

Wear resistance=(amount of wear of Comparative Example 2-1/amount of wear of sample)×100

Low Heat Build-Up

The loss tangent at a temperature of 60° C., tan δ (60° C.), was measured for each of the produced vulcanized rubber sheets using a viscoelastic spectrometer (manufactured by Toyo Seiki Seisaku-sho, Ltd.) under the following conditions: 10% initial distortion, ±2% amplitude, and 20 Hz frequency. The reciprocals of tan δ (60° C.) are shown in Table 1 (low heat build-up). Note that, for Table 1-1, the result was expressed as an index value with the reciprocal of tan δ (60° C.) of Comparative Example 1-1 expressed as an index of 100. Furthermore, for Table 1-2, the result was expressed as an index value with the reciprocal of tan δ (60° C.) of Comparative Example 2-1 expressed as an index of 100. A smaller value indicates superior low heat build-up.

In Tables 1-1 and 1-2 below, the compounded amount of a compound indicates the amount in terms of part by mass of the particular compound or comparative compound used in the synthesis of the modified polymer or comparative modified polymer, per 100 parts by mass of the diene rubber.

Furthermore, in Tables 1-1 and 1-2, the degree of modification indicates the degree of modification of the modified polymer described above.

TABLE 1

| Table 1-1 | Comparative Example 1-1 | Comparative Example 1-2 | Example 1-1 | Example 1-2 | Example 1-3 | Example 1-4 |
|---|---|---|---|---|---|---|
| NR | 85.00 | 85.00 | 85.00 | 85.00 | 85.00 | 85.00 |
| BR | 15.00 | | | 5.00 | | |
| Comparative modified polymer 1 | | 15.00 | | | | |
| Modified polymer 11 | | | 15.00 | | | |
| Modified polymer 12 | | | | 10.00 | 15.00 | |
| Modified polymer 13 | | | | | | 15.00 |
| Carbon black | 50.00 | 50.00 | 50.00 | 50.00 | 50.00 | 50.00 |
| Zinc oxide | 3.00 | 3.00 | 3.00 | 3.00 | 3.00 | 3.00 |
| Steartc acid | 1.50 | 1.50 | 1.50 | 1.50 | 1.50 | 1.50 |
| Peptizing agent | 0.05 | 0.05 | 0.05 | 0.05 | 0.05 | 0.05 |

TABLE 1-continued

| Table 1-1 | Comparative Example 1-1 | Comparative Example 1-2 | Example 1-1 | Example 1-2 | Example 1-3 | Example 1-4 |
|---|---|---|---|---|---|---|
| Anti-aging agent | 1.50 | 1.50 | 1.50 | 1.50 | 1.50 | 1.50 |
| Wax | 1.00 | 1.00 | 1.00 | 1.00 | 1.00 | 1.00 |
| Sulfur | 1.40 | 1.40 | 1.40 | 1.40 | 1.40 | 1.40 |
| Vulcanization accelerator | 1.20 | 1.20 | 1.20 | 1.20 | 1.20 | 1.20 |
| Modification temperature [° C.] | — | 160 | 160 | 160 | 160 | 160 |
| Compounded amount of compound | — | 0.45 | 0.45 | 0.3 | 0.45 | 0.45 |
| Degree of modification | — | 0.38 | 0.25 | 0.15 | 0.15 | 0.08 |
| M100 | 100 | 98 | 104 | 104 | 119 | 111 |
| Wear resistance | 100 | 106 | 108 | 109 | 114 | 115 |
| Low heat build-up | 100 | 98 | 101 | 101 | 102 | 102 |

The details of components shown in Table 1-1 above are as follows.

NR: TSR20
BR: Nipol BR1220 (manufactured by Zeon Corporation)
Comparative modified polymer 1: Comparative modified polymer 1 synthesized as described above
Modified polymer 11: Modified polymer obtained by subjecting BR to modification with a modified polymer 11 (compound represented by Formula (M) (particular compound)) synthesized as described above. Note that n in Formula (M) is 3.
Modified polymer 12: Modified polymer obtained by subjecting BR to modification with a modified polymer 12 (compound represented by Formula (M) (particular compound)) synthesized as described above. Note that n (average value) in Formula (M) is 8.4.
Modified polymer 13: Modified polymer obtained by subjecting BR to modification with a modified polymer 13 (compound represented by Formula (M) (particular compound)) synthesized as described above. Note that n (average value) in Formula (M) is 22.
Carbon black: Show Black N234 (manufactured by Showa Cabot K.K.)
Zinc oxide: Zinc Oxide III (manufactured by Seido Chemical Industry Co., Ltd.)
Stearic acid: Stearic acid YR (manufactured by NOF Corporation)
Peptizing agent: NOCTIZER SD (manufactured by Ouchi Shinko Chemical Industrial Co., Ltd.)
Anti-aging agent: SANTOFLEX 6PPD (manufactured by Soltia Europe)
Wax: SANNOC (manufactured by Ouchi Shinko Chemical Industrial Co., Ltd.)
Sulfur: Oil treatment sulfur (manufactured by Karuizawa Refinery Ltd.)
Vulcanization accelerator: NOCCELER CZ-G (manufactured by Ouchi Shinko Chemical Industrial Co., Ltd.)

TABLE 2

| Table 1-2 | Comparative Example 2-1 | Comparative Example 2-2 | Example 2-1 | Example 2-2 | Example 2-3 |
|---|---|---|---|---|---|
| NR | 16.00 | 16.00 | 16.00 | 16.00 | 16.00 |
| SBR | 98.00 (71) | 49.00 (35.5) | 49.00 (35.5) | 49.00 (35.5) | 49.00 (35.5) |
| BR | 13.00 | 13.00 | 13.00 | 13.00 | 13.00 |
| Comparative modified polymer 2 | | 49.00 (35.5) | | | |
| Modified polymer 21 | | | 49.00 (35.5) | | |
| Modified polymer 22 | | | | 49.00 (35.5) | |
| Modified polymer 23 | | | | | 49.00 (35.5) |
| Carbon black | 20.00 | 20.00 | 20.00 | 20.00 | 20.00 |
| Silica | 60.00 | 60.00 | 60.00 | 60.00 | 60.00 |
| Stearic acid | 2.00 | 2.00 | 2.00 | 2.00 | 2.00 |
| Processing aid | 2.00 | 2.00 | 2.00 | 2.00 | 2.00 |
| Anti-aging agent | 3.00 | 3.00 | 3.00 | 3.00 | 3.00 |
| Wax | 1.00 | 1.00 | 1.00 | 1.00 | 1.00 |
| Coupling agent | 4.80 | 4.80 | 4.80 | 4.80 | 4.80 |
| Oil | 16.17 | 16.17 | 16.17 | 16.17 | 16.17 |
| Zinc oxide | 3.00 | 3.00 | 3.00 | 3.00 | 3.00 |
| Sulfur | 1.85 | 1.85 | 1.85 | 1.85 | 1.85 |
| Vulcanization accelerator CZ | 2.30 | 2.30 | 2.30 | 2.30 | 2.30 |
| Vulcanization accelerator DPG | 0.65 | 0.65 | 0.65 | 0.65 | 0.65 |
| Modification temperature [° C.] | — | 160 | 160 | 160 | 160 |
| Compounded amount of compound | — | 0.30 | 0.30 | 0.30 | 0.30 |
| Degree of modification | — | 0.19 | 0.12 | 0.07 | 0.04 |
| M100 | 100 | 96 | 101 | 105 | 100 |
| Wear resistance | 100 | 108 | 112 | 118 | 116 |
| Low heat build-up | 100 | 99 | 102 | 103 | 102 |

The details of components shown in Table 1-2 above are as follows.

NR: TSR20
SBR: E580 (solution-polymerized SBR; styrene unit content: 37 mass %; vinyl bond content: 43%; oil extended product (oil extender content: 37.5 mass %), manufactured by Asahi Kasei Chemicals Corporation)
BR: Nipol BR1220 (manufactured by Zeon Corporation)
Comparative modified polymer 2: Comparative modified polymer 2 synthesized as described above
Modified polymer 21: Modified polymer obtained by subjecting SBR to modification with a modified polymer 21 (compound represented by Formula (M) (particular compound)) synthesized as described above. Note that n in Formula (M) is 3.
Modified polymer 22: Modified polymer obtained by subjecting SBR to modification with a modified polymer 22 (compound represented by Formula (M) (particular compound)) synthesized as described above. Note that n (average value) in Formula (M) is 8.4.
Modified polymer 23: Modified polymer obtained by subjecting SBR to modification with a modified polymer 23 (compound represented by Formula (M) (particular compound)) synthesized as described above. Note that n (average value) in Formula (M) is 22.

Carbon black: Show Black N339 (manufactured by Cabot Japan K.K.)

Silica: ZEOSIL 165GR (manufactured by Rhodia Silica Korea Co., Ltd.)

Stearic acid: Stearic acid YR (manufactured by NOF Corporation)

Processing aid: Aktiplast ST (manufactured by Rhein Chemie)

Anti-aging agent: SANTOFLEX 6PPD (manufactured by Soltia Europe)

Wax: SANNOC (manufactured by Ouchi Shinko Chemical Industrial Co., Ltd.)

Coupling agent: Si69 (manufactured by Evonik Degussa)

Oil: Extract No. 4S (manufactured by Showa Shell Sekiyu K.K.)

Zinc oxide: Zinc Oxide III (manufactured by Seido Chemical Industry Co., Ltd.)

Sulfur: Oil treatment sulfur (manufactured by Karuizawa Refinery Ltd.)

Vulcanization accelerator CZ: NOCCELER CZ-G (manufactured by Ouchi Shinko Chemical Industrial Co., Ltd.)

Vulcanization accelerator DPG: Soxinol D-G (manufactured by Sumitomo Chemical Co., Ltd.)

As is clear from Tables 1-1 and 1-2, Examples 1-1 to 1-4 which included the modified polymer obtained by modification with the compound represented by Formula (M) above (particular compound) exhibited excellent rigidity, wear resistance, and low heat build-up.

From the comparison among Examples 1-1, 1-3, and 1-4, Examples 1-3 and 1-4 in which the particular compound was a compound obtained by reacting a nitrone compound with at least one type of polyether selected from the group consisting of polyethylene glycol and polypropylene glycol and a molecular weight of the polyether was 400 or greater exhibited even better rigidity. Among these, Example 1-3, in which the molecular weight of the polyether was 1000 or less, exhibited even better rigidity.

From the comparison between Examples 1-2 and 1-3, Example 1-3, in which the content of the modified polymer in the diene rubber was 12 mass % or greater, exhibited even better rigidity, wear resistance, and low heat build-up.

Similarly, Examples 2-1 to 2-3 which included the modified polymer obtained by modification with the particular compound exhibited excellent rigidity, wear resistance, and low heat build-up. Among these, Examples 2-2 and 2-3 in which the particular compound was a compound obtained by reacting a nitrone compound with at least one type of polyether selected from the group consisting of polyethylene glycol and polypropylene glycol and a molecular weight of the polyether was 400 or greater exhibited even better rigidity. Among these, Example 2-2, in which the molecular weight of the polyether was 1000 or less, exhibited even better rigidity.

On the other hand, for Comparative Examples 1-1 and 1-2 and 2-1 and 2-2 which did not include the modified polymer obtained by modification with the particular compound, at least one of the rigidity, wear resistance, or low heat build-up was insufficient.

A rubber composition was prepared by synthesizing a particular compound and a modified polymer in accordance with the same procedure as those for Examples 1-1 to 1-4 and 2-1 to 2-3 except for using polypropylene glycol in place of the polyethylene glycol in the synthesis of the particular compound. When evaluations thereof were performed in the same manner, the similar results described in Tables 1-1 and 1-2 were obtained.

REFERENCE SIGNS LIST

1 Bead portion
2 Sidewall portion
3 Tire tread portion
4 Carcass layer
5 Bead core
6 Bead filler
7 Belt layer
8 Rim cushion

The invention claimed is:

1. A compound represented by Formula (M) below:

[Chemical Formula 1]

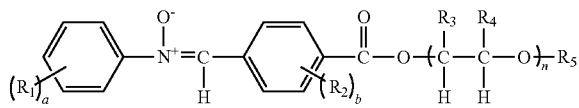

wherein, $R_1$ and $R_2$ each independently represent a substituent; $R_3$ and $R_4$ represent a hydrogen atom or a methyl group; however, if $R_3$ is a methyl group, $R_4$ represents a hydrogen atom, and if $R_4$ is a methyl group, $R_3$ represents a hydrogen atom; $R_5$ represents a hydrogen atom or a hydrocarbon group; a represents an integer of 0 or 1 to 5; b represents an integer of 0 or 1 to 4; and n represents a number of 2 or greater.

2. The compound according to claim 1, wherein the compound is obtained by reacting a nitrone compound with at least one type of polyether selected from the group consisting of polyethylene glycol and polypropylene glycol, and a molecular weight of the polyether is from 150 to 2000.

3. A modified polymer obtained by subjecting a polymer to modification with the compound described in claim 1.

4. The modified polymer according to claim 3, wherein the polymer is at least one type of conjugated diene polymer selected from the group consisting of SBR, BR, IR, NR, and NBR.

5. A rubber composition comprising the modified polymer described in claim 3.

6. The rubber composition according to claim 5, wherein
the rubber composition comprises a diene rubber and a carbon black;
the diene rubber comprises the modified polymer; and
a content of the modified polymer in the diene rubber is from 15 to 70 mass %.

7. A tire produced by using the rubber composition described in claim 5.

8. A conveyor belt produced by using the rubber composition described in claim 5.

9. A modified polymer obtained by subjecting a polymer to modification with the compound described in claim 2.

10. The modified polymer according to claim 9, wherein the polymer is at least one type of conjugated diene polymer selected from the group consisting of SBR, BR, IR, NR, and NBR.

11. A rubber composition comprising the modified polymer described in claim 4.

12. A rubber composition comprising the modified polymer described in claim 9.

13. A rubber composition comprising the modified polymer described in claim 10.

14. The rubber composition according to claim 11, wherein
the rubber composition comprises a diene rubber and a carbon black;
the diene rubber comprises the modified polymer; and
a content of the modified polymer in the diene rubber is from 15 to 70 mass %.

15. The rubber composition according to claim 12, wherein
the rubber composition comprises a diene rubber and a carbon black;
the diene rubber comprises the modified polymer; and
a content of the modified polymer in the diene rubber is from 15 to 70 mass %.

16. The rubber composition according to claim 13, wherein
the rubber composition comprises a diene rubber and a carbon black;
the diene rubber comprises the modified polymer; and
a content of the modified polymer in the diene rubber is from 15 to 70 mass %.

17. A tire produced by using the rubber composition described in claim 6.

18. A tire produced by using the rubber composition described in claim 11.

19. A tire produced by using the rubber composition described in claim 12.

20. A tire produced by using the rubber composition described in claim 13.

* * * * *